(12) United States Patent
Jertson (10) Patent No.: US 7,735,376 B2
(45) Date of Patent: Jun. 15, 2010

(54) SHAFT TORQUE PROFILING APPARATUSES AND METHODS OF USE

(75) Inventor: Marty R. Jertson, Cave Creek, AZ (US)

(73) Assignee: Karsten Manufacturing Corporation, Phoenix, AZ (US)

( * ) Notice: Subject to any disclaimer, the term of this patent is extended or adjusted under 35 U.S.C. 154(b) by 307 days.

(21) Appl. No.: 11/853,205

(22) Filed: Sep. 11, 2007

(65) Prior Publication Data

US 2009/0114034 A1     May 7, 2009

(51) Int. Cl.
*G01N 3/32* (2006.01)
(52) U.S. Cl. .......................... 73/814; 73/65.03
(58) Field of Classification Search ........... 73/760–860, 73/65.01–65.03
See application file for complete search history.

(56) References Cited

U.S. PATENT DOCUMENTS

| | | | |
|---|---|---|---|
| 1,831,320 A | 11/1931 | Pertz | |
| 3,608,366 A | 9/1971 | Tokita et al. | |
| 3,693,402 A | 9/1972 | Jones | |
| 3,718,028 A | 2/1973 | Moser et al. | |
| 3,772,913 A | 11/1973 | Zell et al. | |
| 3,791,203 A | 2/1974 | Rice | |
| 3,850,030 A * | 11/1974 | Adler | 73/862.339 |
| 3,921,045 A * | 11/1975 | Reich et al. | 318/127 |
| 4,003,247 A | 1/1977 | Moser et al. | |
| 4,261,566 A * | 4/1981 | MacDougall | 473/289 |
| 4,270,753 A * | 6/1981 | Maroth et al. | 473/233 |
| 5,247,839 A * | 9/1993 | Okutani et al. | 73/862.326 |
| 5,731,524 A * | 3/1998 | Matsumoto et al. | 73/814 |
| 5,814,773 A * | 9/1998 | Latiri | 177/171 |
| 6,405,595 B1 * | 6/2002 | Harrison | 73/573 |
| 6,477,899 B2 * | 11/2002 | Weiss et al. | 73/579 |
| 6,526,613 B1 * | 3/2003 | Penley | 73/65.03 |
| 6,571,640 B2 | 6/2003 | Harrison | |
| 7,367,238 B2 * | 5/2008 | Hanks | 73/856 |
| 7,578,172 B2 * | 8/2009 | Cho | 73/54.24 |

* cited by examiner

*Primary Examiner*—Max Noori (57) ABSTRACT

Embodiments of shaft torque profiling apparatuses and methods of use are generally described herein. In one embodiment, a method for determining the torsional stiffness of a least a portion of a shaft comprises: immobilizing a first portion of the shaft; immobilizing a second portion of the shaft to define a first region between the first portion and the second portion; rotating a first portion of the first region about an axis of the shaft; and measuring a rotation of the first portion of the first region. Other embodiments herein may be described and claimed.

27 Claims, 8 Drawing Sheets

SHAFT TORQUE PROFILING APPARATUSES AND METHODS OF USE

TECHNICAL FIELD

This disclosure relates generally to characterizing an object and relates more particularly to apparatuses and methods of using the apparatuses to determine torsional characteristics of a shaft.

BACKGROUND

Golf club shafts have been designed to accommodate the preferences of a golfer as well as the golfer's ability. For example, golf club shafts have evolved from wood, to steel, and to composites such as graphite and alloys. Different types of equipment have been developed to empirically measure the various characteristics of golf club shafts, such as stiffness. To further characterize the shaft, however, an apparatus and method to characterize discrete sections of the golf club shaft is desirable.

For simplicity and clarity of illustration, the drawing figures illustrate the general manner of construction, and descriptions and details of well-known features and techniques may be omitted to avoid unnecessarily obscuring shaft torque profiling apparatuses and their methods of use. Additionally, elements in the drawing figures are not necessarily drawn to scale. For example, the dimensions of some of the elements in the figures may be exaggerated relative to other elements to help improve understanding of embodiments of shaft torque profiling apparatuses and their methods of use. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of shaft torque profiling apparatuses and their methods of use described herein are, for example, capable of operation in sequences other than those illustrated or otherwise described herein. Furthermore, the terms "contain," "include," and "have," and any variations thereof, are intended to cover a non-exclusive inclusion, such that a process, method, article, or apparatus that comprises a list of elements is not necessarily limited to those elements, but may include other elements not expressly listed or inherent to such process, method, article, or apparatus.

The terms "left," "right," "front," "back," "top," "bottom," "side," "under," "over," and the like in the description and in the claims, if any, are used for descriptive purposes and not necessarily for describing permanent relative positions. It is to be understood that the terms so used are interchangeable under appropriate circumstances such that the embodiments of shaft torque profiling apparatuses and their methods of use described herein are, for example, capable of operation in other orientations than those illustrated or otherwise described herein. The term "coupled," as used herein, is defined as directly or indirectly connected in a physical, mechanical, electrical, magnetic or other manner.

DESCRIPTION OF EXAMPLES OF EMBODIMENTS

In an exemplary embodiment of shaft torque profiling apparatuses and their methods of use, an exemplary apparatus can comprise: a clamp coupled to a shaft at one position, and another clamp coupled to the shaft at a second position to define a region between the two positions; at least one mass coupled to the shaft within the region; a mass actuator to displace the mass by an angular displacement about an axis of the shaft; and at least one sensor for measuring a frequency of oscillation of the mass.

In another exemplary embodiment of a shaft torque profiling apparatus and their methods of use, an exemplary method can comprise: immobilizing one portion of a shaft, and immobilizing a second portion of the shaft to define a region between the two portions; rotating one portion of the region about an axis of the shaft; and measuring the rotation of the portion of the region.

In another exemplary embodiment of shaft torque profiling apparatuses and their methods of use, an exemplary method can comprise: immobilizing a portion of a shaft; rotating one portion of one region about an axis of the shaft; rotating one portion of a second region about the axis of the shaft; measuring the rotation of the portion of the first region; and measuring the rotation of the portion of the second region.

Figure 1:
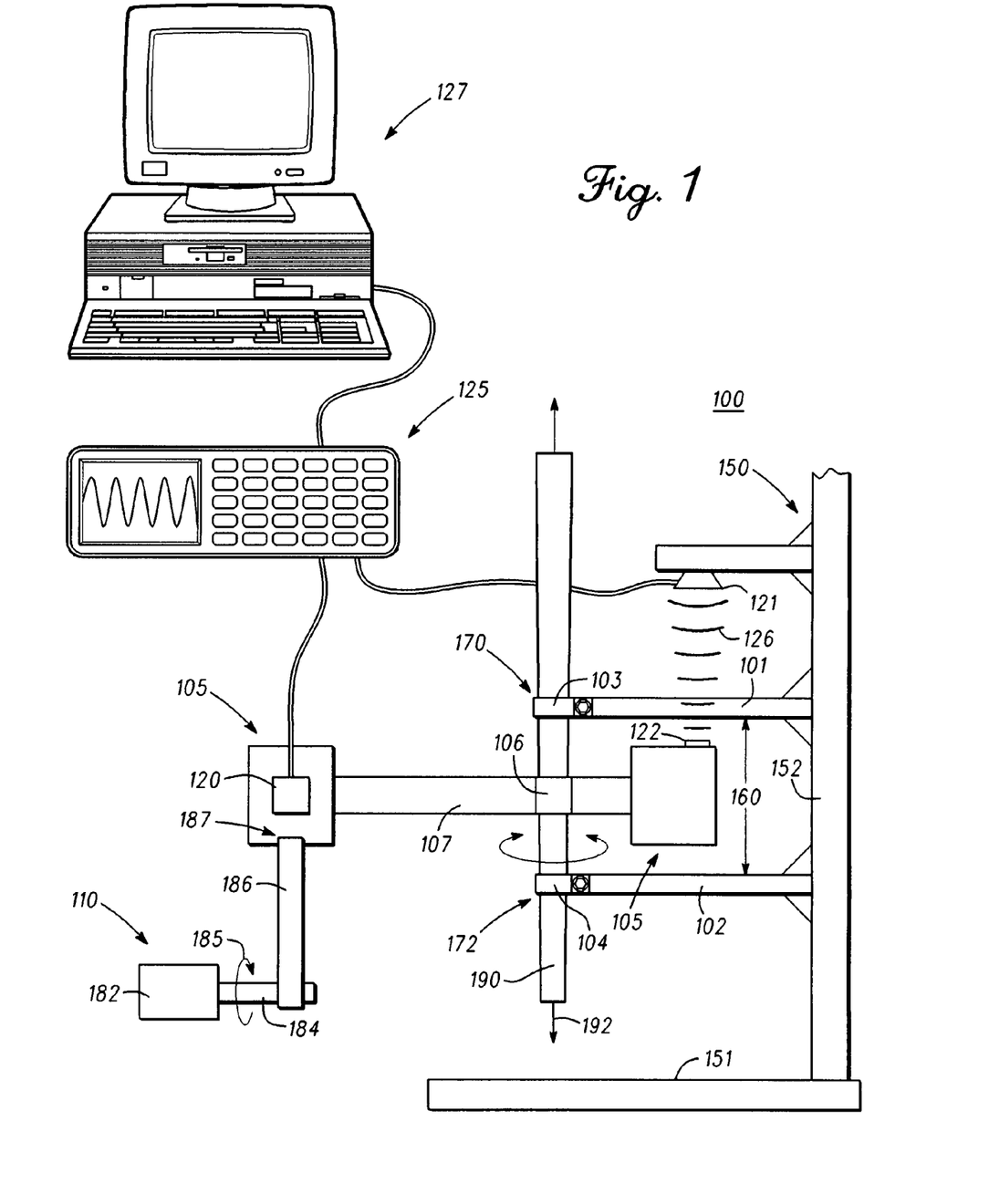
FIG. 1 illustrates a front view of an exemplary shaft torque profiling apparatus according to a first embodiment of the shaft torque profiling apparatuses and methods of their use described herein.

Turning now to the figures, FIG. 1 illustrates an exemplary embodiment of the shaft torque profiling apparatuses and methods of use described herein. In particular, an apparatus 100 determines a torsional stiffness of a portion of a shaft 190 and comprises: a clamp 103 coupled to shaft 190 at a position 170; another clamp 104 coupled to shaft 190 at a position 172 to define a region 160 between position 170 and position 172. Apparatus 100 further comprises: at least one mass 105 coupled to shaft 190 within region 160; a mass actuator 110 to displace mass 105 by an angular displacement 209 (FIG. 2) about an axis 192 of shaft 190; and at least one sensor 120 to measure a frequency of oscillation of mass 105.

Figure 2:
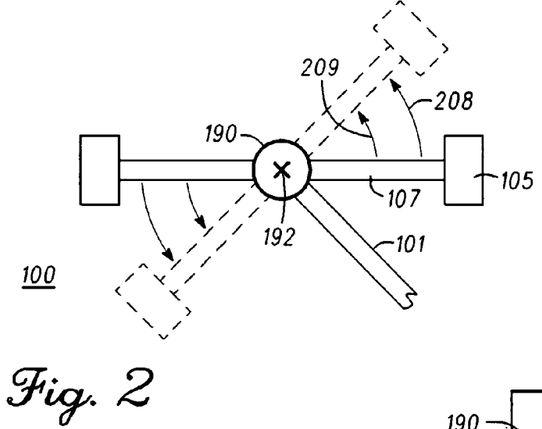
FIG. 2 illustrates a top down view of a portion of the exemplary shaft torque profiling apparatus of FIG. 1.

In this exemplary embodiment, and others described herein, mass 105 can be displaced by mass actuator 110 by angular displacement 209, which is shown by FIG. 2. Mass actuator 110, which will be discussed in greater detail below, displaces mass 105 by angular displacement 209 in a first direction 208, as also shown in FIG. 2. In this manner, after mass 105 is displaced, it can be subsequently released, and the torsional stiffness of shaft 190 at the portion of shaft 190 where mass 105 is coupled, reacts in a torsional, spring-like manner to recoil mass 105 back to its initial position and beyond, thus resulting in a responsive torsional oscillation by mass 105. Among the various embodiments discussed herein, angular displacement 209 can comprise any angle such that torsional oscillations can be introduced. Moreover, while mass 105 is illustrated as being displaced in first direction 208, other directions are likewise contemplated by this disclosure.

Figure 4:
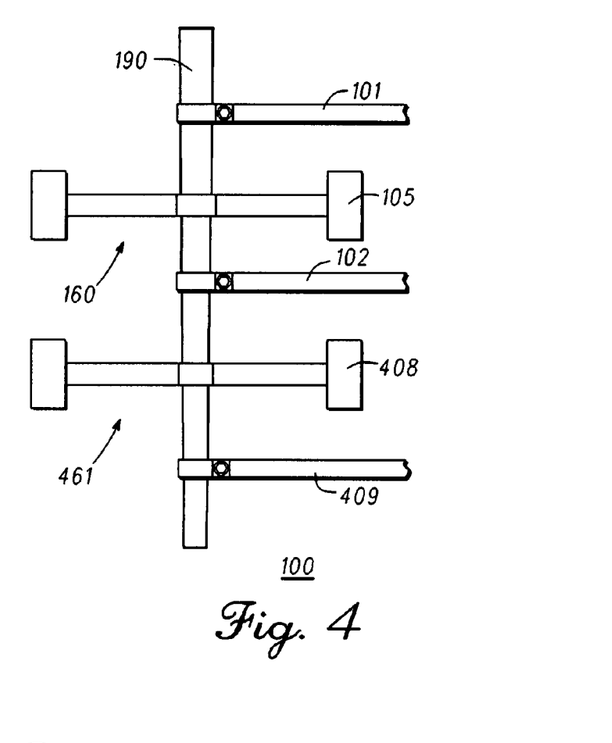
Figure 5:
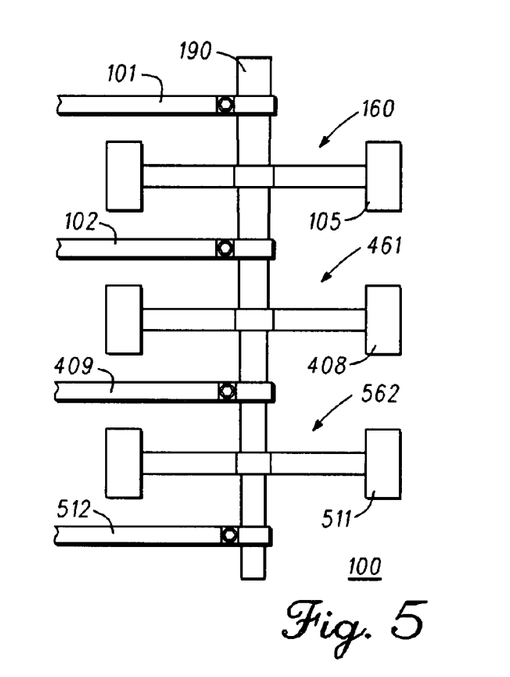

Among the various embodiments discussed herein, and with momentary reference to FIGS. 4-8, it can also be seen that more than one mass can be angularly displaced. For example, FIG. 4 shows mass 105 and a second mass 408. FIG. 5 shows one mass 105, second mass 408, and a third mass 511, etc. Among these various embodiments, such multiple masses can be displaced simultaneously or at offset or overlapping times. For example, one mass may be displaced and released, and a second (or "n" numbers of masses) can be angularly displaced and released at different times. Also, various masses can be displaced by similar angular displacements or at variable angular displacements. For example, all exemplary masses can be displaced 5 degrees, or one mass can be displaced 5 degrees and a second mass can be displaced 10 degrees, etc., and such angular displacements can be in the same direction or opposite directions. In sum, any permutations regarding the number of masses that can be angularly displaced, the degree to which the masses can be angularly displaced, the direction in which the masses can be angularly displaced, and/or the timing of the angular displacements of the masses, are contemplated by this disclosure.

Returning now to FIG. 1, and as briefly mentioned earlier, apparatus 100 comprises mass actuator 110. Mass actuator 110 comprises an exemplary configuration that can angularly displace mass 105 about shaft axis 192. In this exemplary embodiment, mass actuator 110 comprises a motor 182 coupled to an armature 184. Motor 182, when actuated, can turn armature 184 in a direction 185. Another armature 186 can be coupled to armature 184, and as motor 182 rotates as mature 184, motor 182 can likewise rotate armature 186 in the same direction. As shown in FIG. 1, armature 186 can contact mass 105 at a point 187. As armature 186 rotates, contact point 187 can "traverse" along or down the surface of mass 105, thereby "pushing" mass 105 about shaft axis 192 by angular displacement 209 (FIG. 2). Once armature 186 "slips" off of mass 105, mass 105 can subsequently oscillate, as described previously.

Among the various embodiments described herein, mass actuator 110 can embody several different configurations. For example, with reference to the exemplary embodiment shown in FIG. 1, the arrangement of armatures can be organized in different fashions. For example, instead of armature 186 contacting mass 105 at point 187, which is shown towards the bottom portion of mass 105, contact point 187 may contact a side or an edge portion of mass 105, or armature 186 can contact a top portion of mass 105. Additionally, mass actuator 110 can comprise multiple armatures or different configurations to angularly displace multiple masses, i.e., such multiple masses as shown in FIGS. 4-8. Indeed, any configuration of mechanical elements to angularly displace mass 105 (and/or other masses) is contemplated by this disclosure.

Furthermore, mass actuator 110 is described by the exemplary embodiments herein to comprise a mechanical manner to angularly displace mass 105. Other mechanical configurations, however, are also contemplated by this disclosure to angularly displace mass 105. For example, mass 105 can comprise a polarized metallic element, and another polarized element can magnetically displace mass 105, either in a repulsive or attractive fashion. In any event, different exemplary embodiments to angularly displace mass 105, are contemplated by this disclosure.

With continued reference to FIG. 1, in this exemplary embodiment, apparatus 100 further comprises a frame 150 to rigidly mount, for example, clamp 103 and clamp 104. In this exemplary embodiment, clamp 103 can be coupled to frame 150 via an extension member 101. Likewise, clamp 104 can be coupled to frame 150 via an extension member 102. Extension members 101 and 102 can be coupled to frame 150 at a frame member 152, which can be suitably coupled to a frame base 151. The configuration of frame 150 is merely one exemplary embodiment to facilitate securing shaft 190, and other exemplary embodiments are contemplated by this disclosure even though they may not be expressly described.

Among the various exemplary embodiments described herein, clamp 103 and clamp 104 can comprise any type of a clamp or grip that immobilizes shaft 190. The clamps prevent shaft 190 from slipping, turning, and the like as apparatus 100 is operated by a user. For example, various clamps may be used such as, vice grips, compression clamps, pneumatic clamps, C-clamps, and any other like clamps that can be used to secure shaft 190. Moreover, any variation of types of clamps can be used, and a variable numbers of clamps can be used, depending upon a desired configuration by a user to use apparatus 100.

Figure 7:
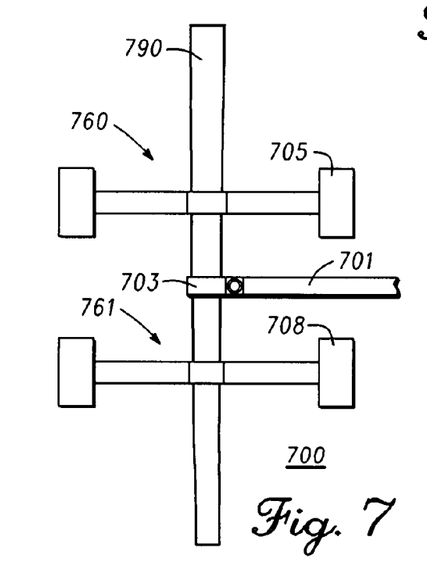
FIGS. 7 and 8 illustrate front views of exemplary configurations of a portion of the exemplary shaft torque profiling apparatus according to a second embodiment.

Next, and as described earlier, clamp 103 can be coupled to shaft 190 at position 170, and clamp 104 can be coupled to shaft 190 at another position 172, wherein the area between the clamps can define region 160. Among various other exemplary embodiments, however, region 160 can comprise variable distances between the clamps depending upon a desired configuration to use apparatus 100. For example, with momentary reference to FIG. 3, region 160 is shown comprising variable regional distances. Among various other exemplary embodiments, the shaft torque profiling apparatuses described herein can also comprise more than one region, which can be seen, for example, among FIGS. 4, 5, 7, and 8. Furthermore, other exemplary regions may not be defined by the distance between clamps, but rather by a relative position to a single clamp. For example, FIG. 7 depicts a shaft 790 clamped via an extension member 701 with a clamp 703. In this exemplary configuration, one region 760 can comprise a portion along the shaft 790 on one side of clamp 703, and another region 761 can comprise another portion along shaft 790 on the opposite side of clamp 703.

Returning to FIG. 1, apparatus 100 comprises at least one mass 105. Mass 105, in this exemplary embodiment, comprises a "dumbbell" type configuration, and mass 105 can be securely coupled to shaft 190 at a shaft portion 106. In this exemplary configuration, mass 105 can be coupled using various clamping or griping mechanisms, such as, for example, those described previously for clamps 103 and 104. Mass 105 can be secured via a mass extension arm 107. In this exemplary configuration, having mass 105 indirectly coupled to shaft 190 via mass extension arm 107, facilitates actuating mass 105 by mass actuator 110, and also to couple sensors, for example sensor 120. Mass 105, in this exemplary embodiment, provides the mass that can operate as the torsional pendulum, and the oscillatory behavior of mass 105 can be measured to deduce the torsional stiffness for shaft 190 at shaft portion 106.

The exemplary embodiment shown in FIG. 1 illustrates one configuration for mass 105, but different masses are contemplated by this disclosure, as well as additional numbers of masses. For example, and as briefly disclosed earlier, the apparatuses described herein can comprises more than one mass. With momentary reference to FIGS. 4-8, a variable number of masses are shown. These masses can be similar (as shown) or they can be different. For example, the exemplary masses shown in FIGS. 4-8 can comprise 10 kilograms (kg), or one mass can comprise 5 kg and another mass can comprise 10 kg, etc.

Among the exemplary embodiments illustrated in FIGS. 1-8, the various masses are shown as being symmetric with respect to the shaft, but different embodiments can comprise non-symmetric configurations. For example, and with reference to FIG. 9, one exemplary embodiment shows a mass 905 that is non-symmetrical about shaft 190. Moreover, the various embodiments disclosed herein show the masses as comprising a "dumbbell" type configuration, and also, as in FIG. 9, mass 905 comprises a "one-half dumbbell" type configuration. However, any mass can be used if it can be coupled to the shaft such that the mass can operate as a torsional pendulum so the torsional stiffness of the shaft can be determined by such mass. For example, and with momentary reference to FIG. 10, toroid mass 1005 is shown coupled to the shaft 1090. Toroid mass 1005 can be segmented or separated into two or more discrete portions.

Continuing with the exemplary embodiment as shown in FIG. 1, apparatus 100 comprises sensor 120 to measure the position of mass 105 with respect to time as mass 105 oscillates. In this exemplary embodiment, sensor 120 comprises an accelerometer to measure the acceleration and de-acceleration of mass 105 as it oscillates. Accelerometer sensor 120 can be coupled to mass 105, and the detected acceleration and de-acceleration measurements can be output to an electronic device configured to receive such data signals, for example an oscilloscope 125. Among the various embodiments described herein, sensor 120 can comprise sensors to measure not only time, position, and acceleration, but sensors to measure, velocity, momentum, and the like are similarly contemplated by this disclosure.

Moreover, this disclosure likewise contemplates sensors other than the exemplary sensor described above. For example, and with continued reference to FIG. 1, a sensor element 121 can comprise a photo eye that can transmit a light signal 126 to a reflective element 122. Reflective element 122 can be coupled to mass 105, and as mass 105 oscillates, light signal 126 is periodically reflected back to photo eye 121. In this manner, photo eye 121 can be electronically coupled to, for example, oscilloscope 125 to also receive oscillation data to subsequently plot time, position, acceleration, etc. of mass 105. The various embodiments described above contemplate coupling the sensors to oscilloscope 125, but the sensors may be similarly coupled to other devices suitable to collect and interpret the signals output by the sensors. For example, sensors 120 and 121 can be directly coupled to a computer system 127.

Continuing with the exemplary embodiment shown in FIG. 1, apparatus 100 comprises computer system 127. Computer system 127 can be suitably coupled to oscilloscope 125 to receive input data received by oscilloscope 125 via sensors 120 and/or 121. As data is transmitted to computer 127, various algorithms can be accessed and used to interpret the data and/or to calculate the torsional stiffness of shaft 190 at, for example, portion 106, where mass 105 is coupled to shaft 190. Moreover, computer system 127 can be further used to carry out other algorithmic functions. For example, computer system 127 can be used to map various torsional stiffnesses at various portions along shaft 190. In this manner, a stiffness profile of shaft 190 can be determined. Among other various embodiments, computer system 127 can be used to determine a stiffness profile that may be subsequently compared with other shafts of different materials, or shafts having different dimensions, or shafts that have been manufactured in different manners. Computer system 127 can be used to determine any number of calculable and/or analytical provisions.

Among the various exemplary embodiments described herein, computer system 127, or any other system as part of the shaft torque profiling apparatus described, can be used to calculate or determine the torsional characteristics of a shaft. For example, one exemplary determination can be Young's Modulus, which is often referred to as a modulus of elasticity, and generally measured in gigapascals (GPa). Other calculations may include determining a spring constant, "K" as a shaft measurement, and such spring constant can be generally expressed as torque per radian, or, for example, Newton-meters per radian (N-m/rad). Young's modulus and the spring constant K are described, however, any other measurements that can be calculated or determined by the shaft torque profiling apparatus described herein, is contemplated by this disclosure.

Figure 11:
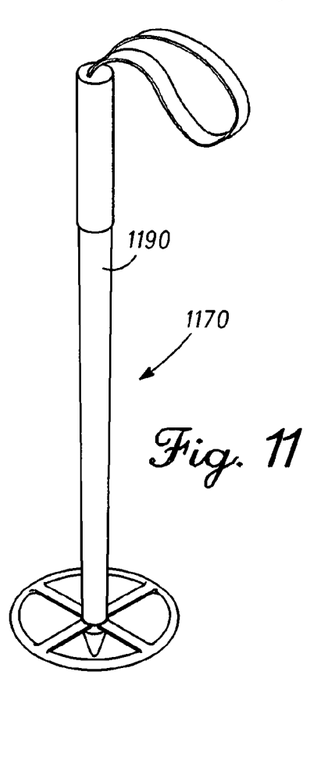
FIGS. 11 and 12 illustrate exemplary sporting goods comprising shafts that can be profiled using the exemplary shaft torque profiling apparatus of FIG. 1.
Figure 12:
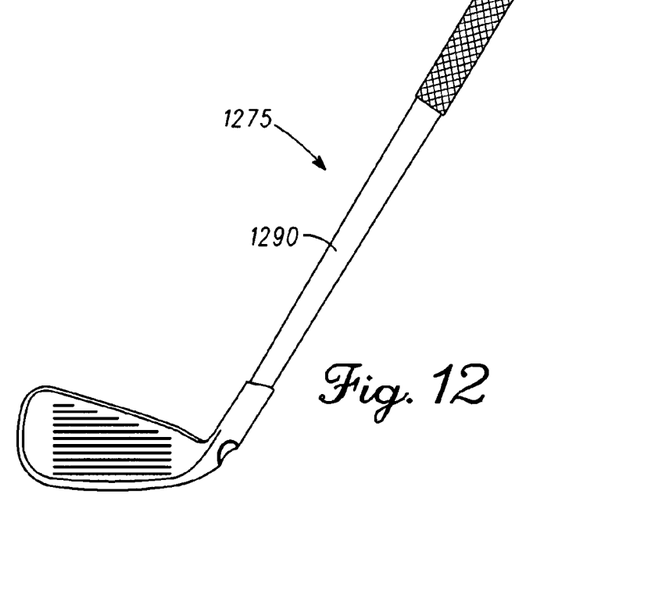

Among the various exemplary embodiments described herein, computer system 127 can be further used to calculate the various stiffnesses of a shaft to accommodate the various preferences of user, for example, the preferences of a golfer with respect to the stiffness determination of a golf club shaft. For example, FIG. 12 shows a golf club 1275 having a golf club shaft 1290. However, the torsional stiffness of other exemplary embodiments of sporting goods can be determined. For example, FIG. 11 shows a ski pole 1170 having a ski pole shaft 1190. Other exemplary sporting good shafts are similarly contemplated by this disclosure.

Figure 3:
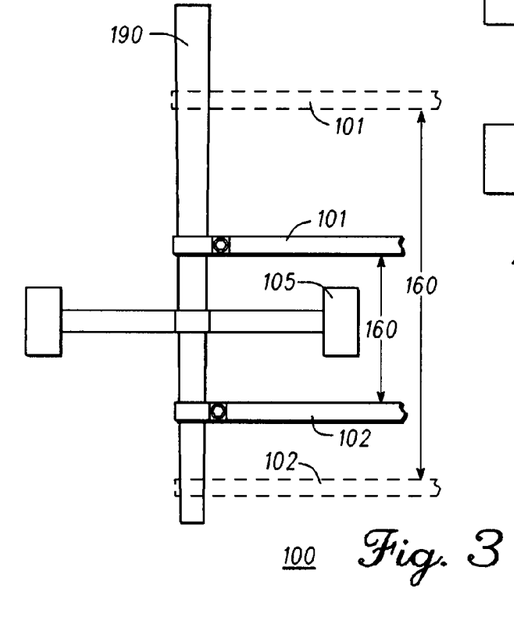
FIGS. 3-6 illustrate front views of exemplary configurations of a portion of the exemplary shaft torque profiling apparatus of FIG. 1.

Among the various exemplary embodiments described herein, apparatus 100 can comprise a configuration to determine the torsional stiffness of shaft 190 solely within region 160 as briefly described above. However, as shown among various exemplary embodiments, for example, as those exemplary embodiments shown among FIGS. 4-8, different configurations are contemplated by this disclosure. Moreover, configurations not shown among the various figures, are similarly contemplated by this disclosure. For example, and with reference to FIG. 4, an exemplary embodiment shows two masses, mass 105, such as shown in FIGS. 1-3, and second mass 408. In this exemplary embodiment, mass 105 can be coupled to shaft 190 within region 160, but second mass 408 can be coupled to shaft 190 within a second region 461, where second region 461 can be defined between extension member 102 and an extension member 409, thereby allowing two separate torsional stiffnesses to be determined at two separate locations of shaft 190.

With reference to FIG. 5, another exemplary embodiment shows a third region, 562, that can be defined between extension member 409 and an extension member 512. Within region 562, a third mass 511 can be coupled to shaft 190 to further determine the torsional stiffness of shaft 190 at a third location. In this manner, and as explained earlier, a user can thereby map the stiffnesses of shaft 190 at various positions, and thus, can determine a stiffness profile of shaft 190.

Figure 6:
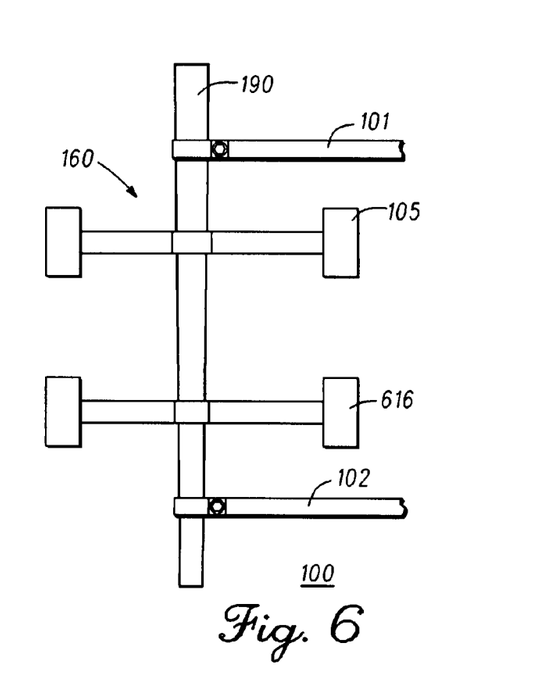

In another exemplary embodiment, a user may desire to determine torsional stiffness of a shaft at more than one location within a single region. With reference to FIG. 6, mass 105 coupled to shaft 190 within region 160 can be further accompanied by a second mass 616 coupled to shaft 190 also within region 160.

Among the various exemplary embodiments discussed so far, mass 105 has been shown as coupled to shaft 190 within region 160 between, for example, extension members 101 and 102. In another exemplary embodiment, and with reference to FIG. 7, a single extension member 701 coupled to shaft 790 bisects shaft into two separate regions, region 760 and region 761. Thus, in this exemplary embodiment, the regions are not defined between extension members, but rather defined with respect to one side or the other of a single extension member, in this case, extension member 701. In this exemplary embodiment, a mass 705 can be coupled to shaft 790 at region 760, and a second mass 708 can be coupled at region 761.

Figure 8:
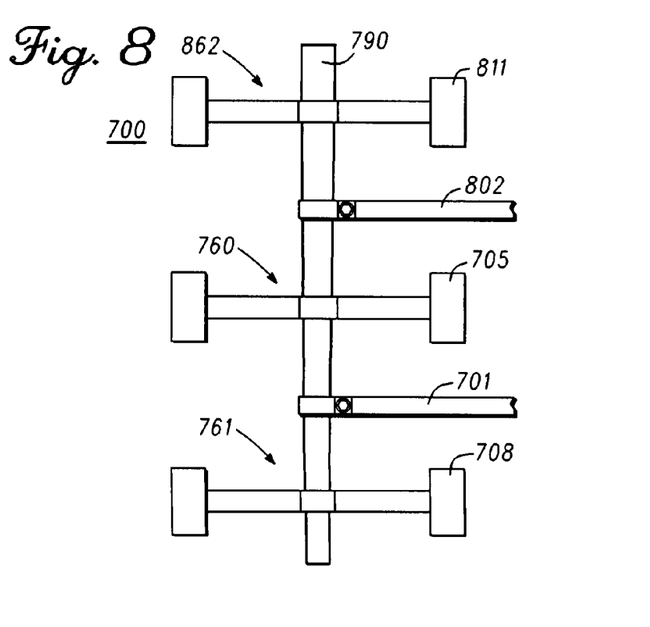

In a continuing exemplary embodiment and with reference to FIG. 8, a third region can be defined, wherein a second extension member 802 can be coupled to shaft 790. In this manner mass 705 can be coupled within region 760 now defined between extension members 701 and 802 rather than merely on one side of a single extension member, such as extension member 701 in FIG. 7. In this continuing exemplary embodiment, second mass 708 can again be coupled to shaft 790 on the other side of extension member 701 at region 761. In this continuing exemplary embodiment, however, a third mass 811 can be coupled to shaft 790 at a third region 862. In this exemplary embodiment, a different manner to couple three masses to three different regions is described, which is different than the three masses coupled to the shaft at three different regions, for example, as shown in FIG. 5. In sum, among the various exemplary embodiments discussed herein, permutations of defined regions and coupled mass configurations are contemplated by this disclosure.

Figure 13:
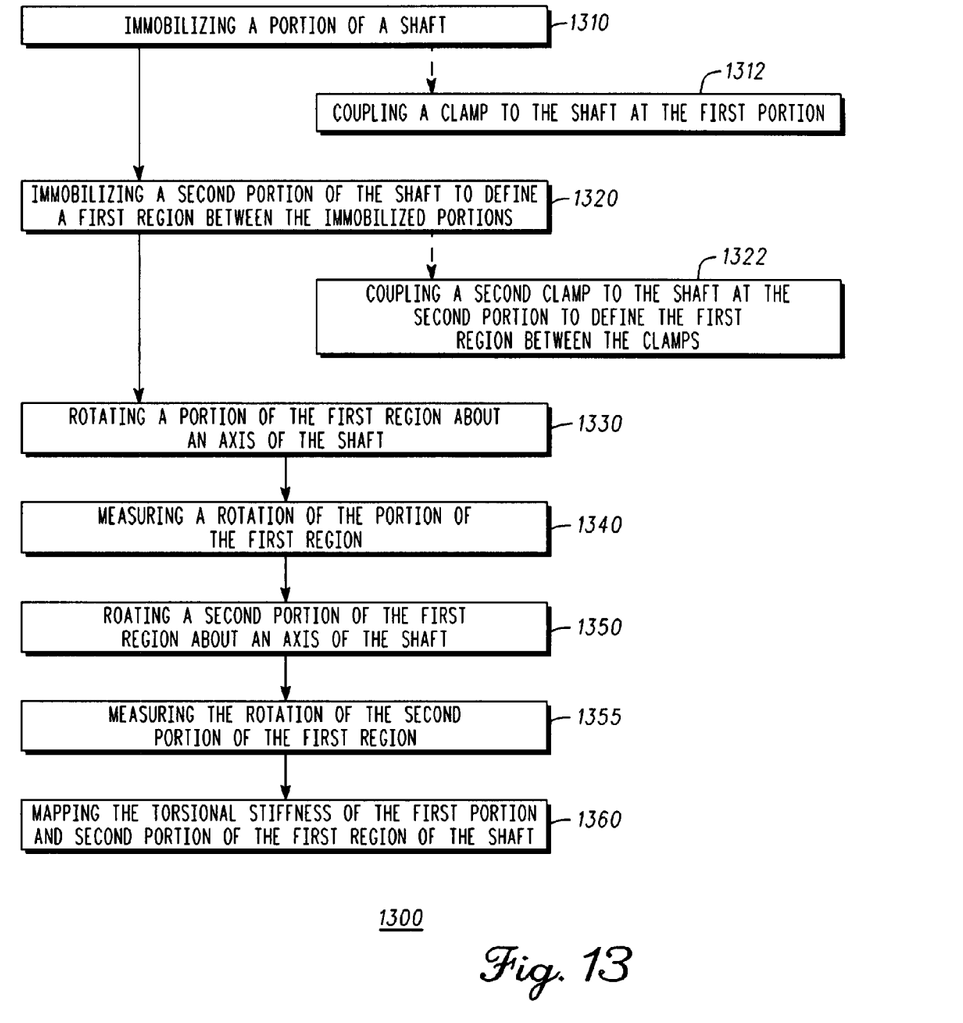
FIGS. 13-18 depicts a flow diagram representation of a manner in which a shaft torque profiling apparatus can be used, according to an embodiment.

In accordance with an exemplary embodiment of shaft torque profiling apparatuses and methods of use, and with reference to FIG. 13, an exemplary method 1300 for determining the torsional stiffness of a portion of a shaft comprises: immobilizing one portion of a shaft (a block 1310); immobilizing an other portion of the shaft to define a first region between the immobilized portions (a block 1320); rotating a portion of the first region about an axis of the shaft (a block 1330); and measuring a rotation of the portion of the first region (a block 1340).

In this exemplary method embodiment, immobilizing one portion of the shaft (block 1310) comprises coupling a clamp to the shaft at the first portion (a block 1312); and immobilizing an other portion of the shaft (block 1320) comprises, coupling a second clamp to the shaft at the other portion (a block 1322).

Figure 14:
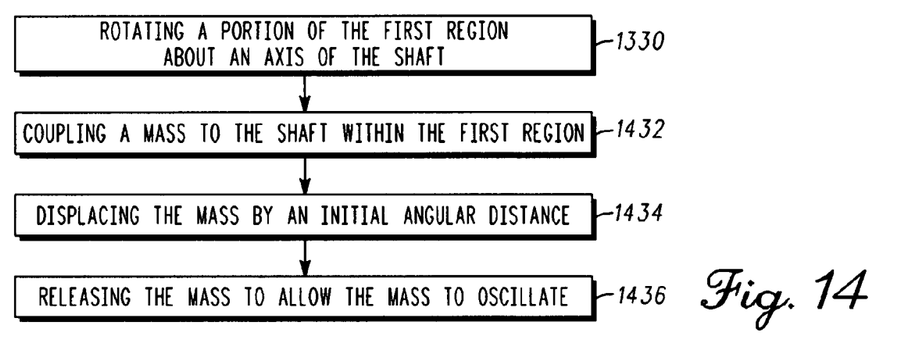

Continuing with this exemplary embodiment, referring to FIGS. 13 and 14 rotating a portion of the first region about an axis of the shaft (block 1330) comprises: coupling a mass to the shaft within the first region (a block 1342); displacing the mass by an initial angular distance (a block 1434); and releasing the mass to allow the mass to oscillate (a block 1436).

Figure 15:
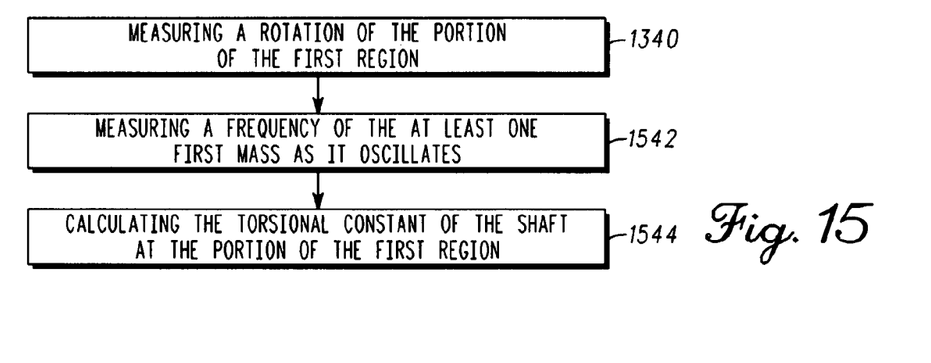

Continuing still with this exemplary embodiment, referring to FIGS. 13 and 15, measuring a rotation of the portion of the first region (block 1340) comprises: measuring a frequency of the mass as it oscillates (a block 1542); and calculating the torsional spring constant of the shaft at the portion of the first region (a block 1544).

In a first continuing exemplary embodiment, referring to FIG. 13, the exemplary method further comprises: rotating a second portion, different than the first portion, of the first region about an axis of the shaft (a block 1350); and measuring a rotation of the second portion of the first region (a block 1355).

Figure 16:
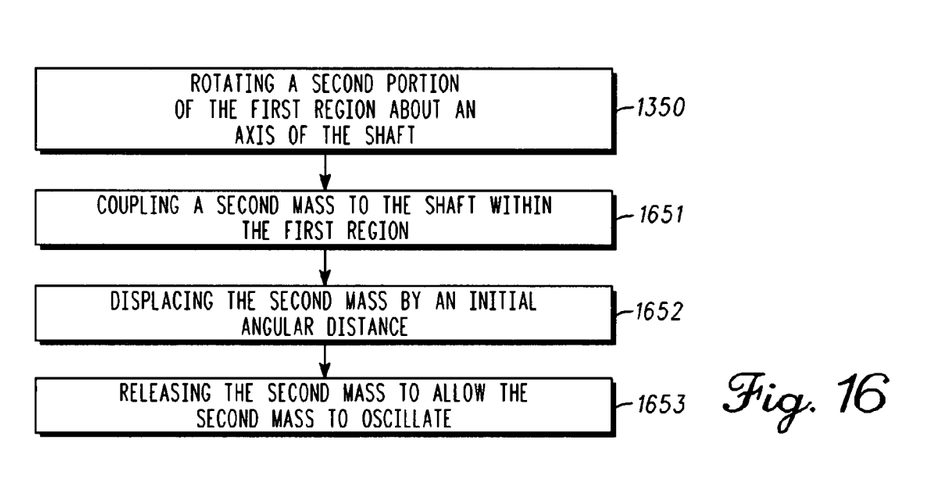

In this first continuing exemplary embodiment, referring to FIGS. 13 and 16, rotating a second portion of the first region about an axis of the shaft (block 1350) comprises: coupling a second mass to the shaft within the first region (a block 1651); displacing the second mass by an initial angular distance (a block 1652); and releasing the second mass to allow the second mass to oscillate (a block 1653).

Figure 17:
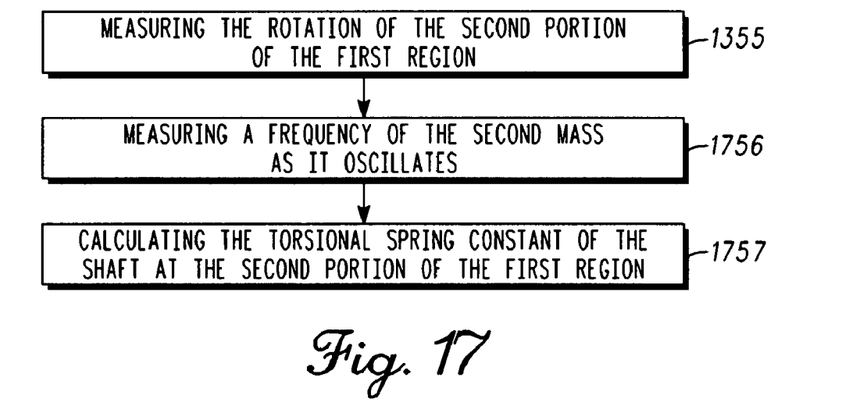

Still further, in this first continuing exemplary embodiment, referring to FIGS. 13 and 17, measuring a rotation of the second portion of the first region (block 1355) comprises: measuring a frequency of the second mass as it oscillates (a block 1756); and calculating the torsional spring constant of the shaft at the second portion of the first region (a block 1757).

As illustrated in FIG. 13, this first continuing exemplary embodiment can further comprise mapping the torsional stiffnesses of the first portion and second portion of the first region of the shaft (a block 1360).

Figure 18:
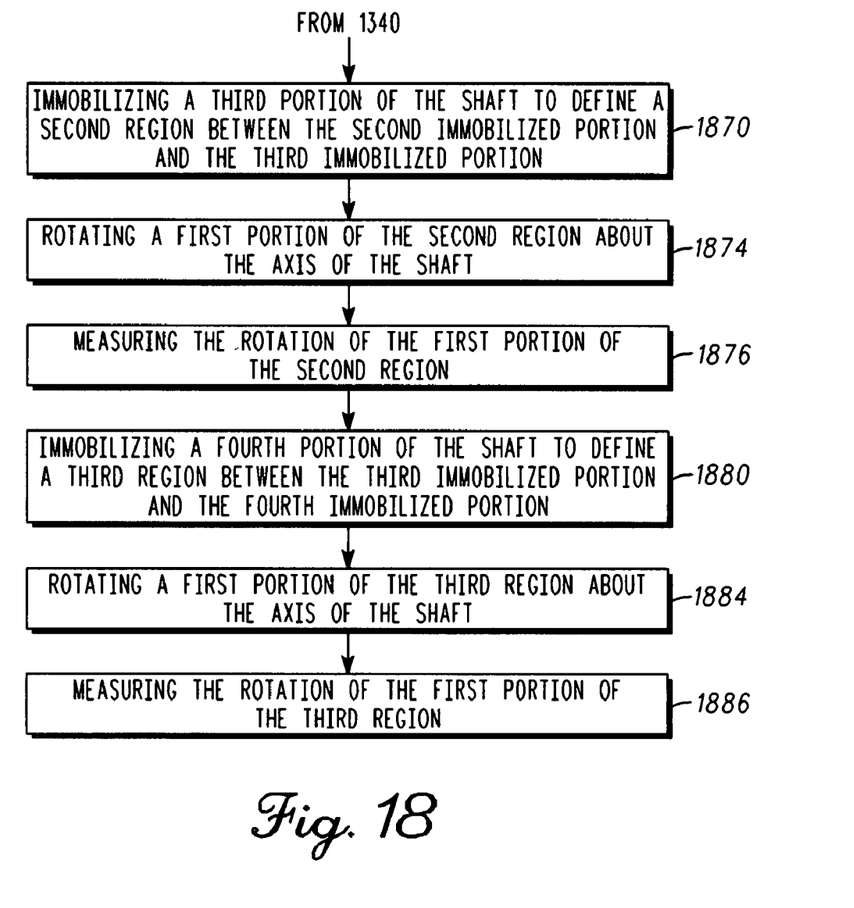

Next, in a second continuing exemplary embodiment, after block 1340, the method for measuring the torsional stiffness of a shaft can further comprise, as illustrated in FIG. 18: immobilizing a third portion of the shaft to define a second region between the second immobilized portion and the third immobilized portion (a block 1870); rotating a portion of the second region about the axis of the shaft (a block 1874); and measuring a rotation of the portion of the second region (a block 1876).

Moreover, the second continuing exemplary embodiment can also further comprise: immobilizing a fourth portion of the shaft to define a third region between the third immobilized portion and the fourth immobilized portion (a block 1880); rotating a portion of the third region about the axis of the shaft (a block 1884); and measuring a rotation of the portion of the third region (a block 1886).

Figure 19:
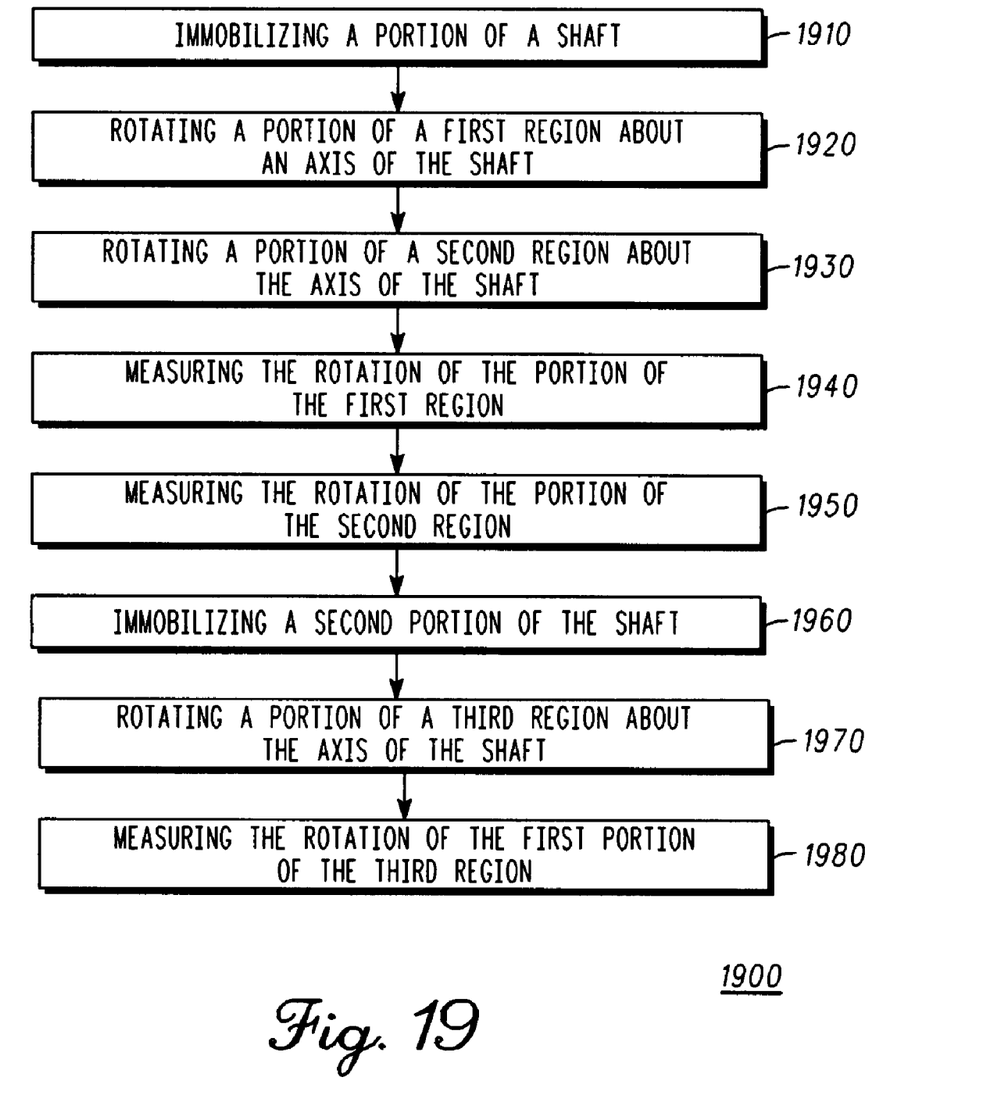
FIG. 19 depicts a flow diagram representation of a manner in which a shaft torque profiling apparatus can be used, according to another embodiment.

Turning now to FIG. 19, another exemplary method 1900 for determining a torsional stiffness of a shaft comprises: immobilizing a first portion of the shaft (a block 1910); rotating a portion of a first region about an axis of the shaft (a block 1920); rotating a portion of a second region about the axis of the shaft (a block 1930); measuring a rotation of the portion of the first region (a block 1940); and measuring a rotation of the portion of the second region (a block 1950).

In this different exemplary embodiment, the method can further comprise: immobilizing a second portion of the shaft (a block 1960); rotating a portion of a third region about the axis of the shaft (a block 1970); and measuring a rotation of the portion of the third region (a block 1980).

Among the various exemplary methods described herein, the first clamp and the second clamp can be similar to the clamps 103 and 104 described earlier and shown in FIG. 1, and may further comprise the various configurations contemplated by clamps 103 and 104, which were earlier disclosed and described. Similarly, the shaft described herein among the various exemplary methods, can be similar to the shaft 190 in FIGS. 1-6 and 9-10, shaft 790 in FIGS. 7-8, shaft 1190 in FIG. 11, and/or shaft 1290 in FIG. 12.

Figure 9:
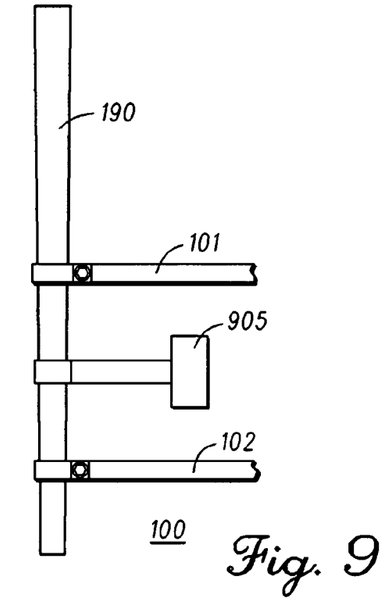
FIGS. 9 and 10 illustrate front view of exemplary configurations of a portion of the exemplary shaft torque profiling apparatus of FIG. 1.
Figure 10:
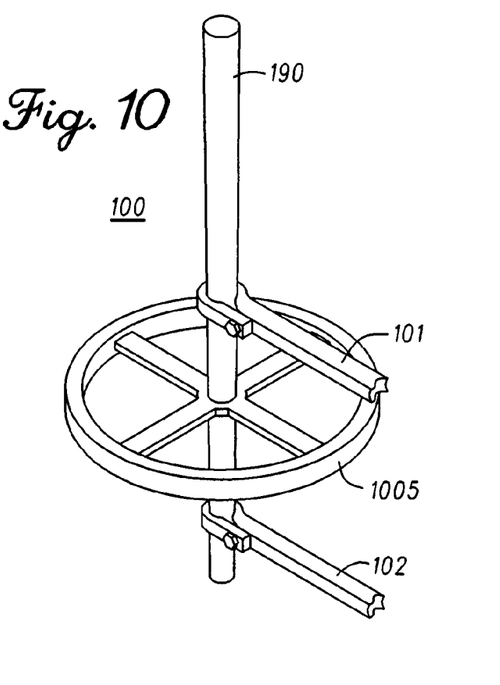

Among the various exemplary methods described herein and the various elements that were disclosed, the first mass, second mass, third mass, etc., can be similar to mass 105 shown and described in FIGS. 1-6, mass 705 in FIGS. 7-8, mass 905 in FIG. 9, and/or mass 1005 in FIG. 10. The first region, second region, third region, etc., can be similar to region 160 shown and described in FIGS. 1 and 3-6, region 760 in FIGS. 7-8, region 461 in FIGS. 4-5, region 761 in FIGS. 7-8, region 562 in FIG. 5, and/or region 862 in FIG. 8. Also, the displaced angular distance can be similar to the angular distance shown in FIG. 2.

Among the exemplary methods described herein, and although a particular order of actions is illustrated in FIGS. 13-19, these actions may be performed in other temporal sequences. For example, the actions depicted in FIGS. 13-19 may be performed sequentially, concurrently, or simultaneously. Additionally, blocks 1350, 1355, and/or 1360 (FIG. 13) can be performed before or after blocks 1870, 1874, and/or 1876 (FIG. 18), and/or blocks 1880, 1884, and/or 1886 (FIG. 18) can be performed before or after blocks 1350, 1355, 1360, 1870, 1874, and/or 1876 (FIGS. 13 and 18). Moreover, as additional examples, the blocks 11410, 1920, 1930, 1940, 1950, 1960, 1920, and/or 1980 (FIG. 19) can be performed before or after the blocks described in FIGS. 13-18. Other variations of exemplary methods are also contemplated by this disclosure.

Additional examples of such changes have been given in the foregoing description. Accordingly, the disclosure of embodiments of shaft torque profiling apparatuses and methods of use is intended to be illustrative of the scope of shaft torque profiling apparatuses and methods of use and is not intended to be limiting. For example, in one embodiment, a shaft torque profiling apparatus may have one or more features of FIG. 1, with or without the features described with reference to FIGS. 3-10. Other permutations of the different embodiments having one or more of the features of the various figures are likewise contemplated. Additionally, the masses of FIGS. 1-10 can be centered or non-centered between the clamps or extension members, and/or the masses of FIGS. 1-10 can be evenly or unevenly spaced apart from each other, the clamps, and/or the extension members. It is intended that the scope of shaft torque profiling apparatuses and methods of use shall be limited only to the extent required by the appended claims.

The shaft torque profiling apparatuses and methods of their use discussed herein may be implemented in a variety of embodiments, and the foregoing discussion of these embodiments does not necessarily represent a complete description of all possible embodiments. For example, in another exemplary embodiment of a shaft torque profiling apparatus, instead of measuring the frequency of oscillation, this disclosure further contemplates twisting a shaft a fixed angle, and then measuring the force necessary for such angular displacement. The force can be measured using, for example, a Load Cell (or like device). The isolated fixturing of the various zones by various clamping configurations described herein can be similar to those discussed, but the stiffness measurement would be done statically, thus providing a similar result, which is the torsional rigidity for a particular isolated zone. In any event, the detailed description of the drawings, and the drawings themselves, disclose at least one preferred embodiment of a shaft torque profiling apparatus and its method of use, and may disclose alternative embodiments of shaft torque profiling apparatuses and their methods of use.

All elements claimed in any particular claim are essential to the shaft torque profiling apparatus and method of use claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An apparatus to determine a torsional stiffness of a portion of a shaft comprising:
   a first clamp coupled to immobilize the shaft at a first position;
   a second clamp coupled to immobilize the shaft at a second position to define a first region between the first position and the second position;
   at least one first mass coupled to the shaft within the first region;
   a mass actuator to displace the at least one first mass by an angular displacement about an axis of the shaft; and
   at least one first sensor for measuring a frequency of oscillation of the at least one first mass.

2. The apparatus of claim 1, further comprising
   a first device to receive an input from the at least one first sensor.

3. The apparatus of claim 2, wherein
   the first device comprises a computer.

4. The apparatus of claim 2, wherein
   the first device comprises an oscilloscope.

5. The apparatus of claim 4, further comprising
   a computer electrically coupled to the oscilloscope to interpret a received signal from the oscilloscope to determine the torsional stiffness of the portion of the shaft.

6. The apparatus of claim 1, further comprising
   a second mass coupled to the shaft within the first region at a different location than the at least one first mass.

7. The apparatus of claim 6, further comprising
   a second sensor for measuring a frequency of oscillation of the second mass.

8. The apparatus of claim 1, wherein
   the at least one first sensor comprises an accelerometer.

9. The apparatus of claim 1, wherein
   the at least one first sensor comprises a photosensor.

10. The apparatus of claim 1, further comprising
    a frame to rigidly mount at least the first clamp and the second clamp.

11. The apparatus of claim 1, wherein the shaft comprises a golf club shaft.

12. The apparatus of claim 1, further comprising:
    a third clamp coupled to the shaft at a third position to define a second region between the second position and the third position;
    a second mass coupled to the shaft within the second region; and
    a second sensor for measuring a second frequency of oscillation of the second mass.

13. An apparatus to determine a torsional stiffness of a portion of a shaft comprising:
    a first clamp coupled to immobilize the shaft at a first position;
    a first mass coupled to the shaft at a first region, the first region located at a first side of the clamp;
    a second mass coupled to the shaft at a second region, the second region located at a second side of the clamp;
    a mass actuator to displace at least the first mass by an angular displacement about an axis of the shaft;
    a first sensor for measuring a frequency of oscillation of the first mass; and
    a second sensor for measuring a frequency of oscillation of the second mass.

14. The apparatus of claim 13, further comprising:
    a second clamp coupled to the shaft at a second position at the first side of the clamp, the first mass located between the first and second clamps;

a third mass coupled to the shaft at a third region, the third region located at a side of the second clamp opposite the first region; and a third sensor for measuring a frequency of oscillation of the third mass.

15. A method for determining torsional stiffness of a portion of a golf club shaft comprising:

immobilizing a first portion of the golf club shaft;

immobilizing a second portion of the golf club shaft to define a first region between the first portion and the second portion;

rotating a first portion of the first region to generate torsion about an axis of the golf club shaft; and measuring a rotation of the first portion of the first region.

16. The method of claim 15, wherein:

immobilizing the first portion of the golf club shaft comprises coupling a first clamp to the golf club shaft at the first portion; and immobilizing the second portion of the golf club shaft comprises coupling a second clamp to the golf club shaft at the second portion to define the first region between the first clamp and the second clamp.

17. The method of claim 16, wherein rotating the first portion of the first region about the axis of the golf club shaft comprises:

coupling at least one mass to the golf club shaft within the first region;

displacing the at least one mass by an initial angular distance; and releasing the at least one mass to allow the at least one mass to oscillate.

18. The method of claim 17, wherein measuring the rotation of the first portion of the first region comprises:

measuring a frequency of the at least one mass as it oscillates; and calculating a torsional spring constant of the golf club shaft at the first portion of the first region.

19. The method of claim 18, further comprises:

rotating a second portion, different than the first portion, of the first region about the axis of the golf club shaft; and measuring a rotation of the second portion of the first region.

20. The method of claim 19, wherein:

rotating the second portion of the first region about the axis of the golf club shaft comprises:

coupling a second mass to the golf club shaft within the first region;

displacing the second mass by an initial angular distance; and releasing the second mass to allow the second mass to oscillate.

21. The method of claim 20, wherein measuring the rotation of the second portion of the first region comprises:

measuring a frequency of the second mass as it oscillates; and calculating a torsional spring constant of the golf club shaft at the second portion of the first region.

22. The method of claim 21 further comprising mapping the torsional stiffnesses of the first portion and the second portion of the first region of the golf club shaft.

23. The method of claim 22, further comprising:

immobilizing a third portion of the golf club shaft to define a second region between the second portion and the third portion;

rotating a first portion of the second region about the axis of the golf club shaft; and measuring a rotation of the first portion of the second region.

24. The method of claim 23, further comprising:

immobilizing a fourth portion of the golf club shaft to define a third region between the third portion and the fourth portion;

rotating a first portion of the third region about the axis of the golf club shaft; and measuring a rotation of the first portion of the third region.

25. A method for determining a torsional stiffness of a shaft comprising:

immobilizing a first portion of the shaft;

rotating a portion of a first region to generate torsion about an axis of the shaft, the portion of the first region located at a first side of the first portion of the shaft;

rotating a portion of a second region to generate torsion about the axis of the shaft, the portion of the second region located at a second side of the first portion of the shaft, the first side opposite the second side;

measuring a rotation of the portion of the first region; and measuring a rotation of the portion of the second region.

26. The apparatus of claim 25, wherein:

the shaft comprises a golf club shaft.

27. The method of claim 13, wherein:

the shaft comprises a golf club shaft.

* * * * *